(12) United States Patent
Avon

(10) Patent No.: US 6,793,640 B1
(45) Date of Patent: Sep. 21, 2004

(54) ANKLE SUPPORT

(76) Inventor: Guy Avon, 1289 Berard, Mascouche, QBC (CA), J7K 2J6

( * ) Notice: Subject to any disclaimer, the term of this patent is extended or adjusted under 35 U.S.C. 154(b) by 0 days.

(21) Appl. No.: 10/465,681

(22) Filed: Jun. 20, 2003

(51) Int. Cl.$^7$ .................................................. A61F 5/00
(52) U.S. Cl. .......................................... 602/23; 602/27
(58) Field of Search ................................ 602/5, 16, 26, 602/27; 128/882

(56) References Cited

U.S. PATENT DOCUMENTS

| | | | |
|---|---|---|---|
| 3,986,501 A | 10/1976 | Schad | |
| 4,289,122 A | 9/1981 | Mason et al. | |
| 4,517,968 A | 5/1985 | Greene et al. | |
| 4,523,394 A | 6/1985 | Lindh et al. | |
| 4,646,726 A | 3/1987 | Westin et al. | |
| 4,955,370 A | 9/1990 | Pettine | |
| 4,982,733 A | 1/1991 | Broadhurst et al. | |
| 5,090,138 A | * 2/1992 | Borden .......................... | 26/102 |
| 5,219,324 A | 6/1993 | Hall | |
| 5,376,068 A | 12/1994 | Grifka | |
| 5,449,005 A | 9/1995 | Echols | |
| 5,496,263 A | * 3/1996 | Fuller ............................ | 602/27 |
| 5,527,269 A | 6/1996 | Reithofer | |
| 5,700,237 A | 12/1997 | Hess | |
| 5,759,168 A | * 6/1998 | Bussell .......................... | 602/27 |
| 5,951,504 A | 9/1999 | Iglesias et al. | |
| 5,966,843 A | * 10/1999 | Sand ............................ | 36/717.1 |
| 5,971,946 A | * 10/1999 | Quinn ............................ | 602/27 |
| 6,083,184 A | 7/2000 | Kenosh | |
| 6,102,881 A | 8/2000 | Quackenbush et al. | |
| 6,267,742 B1 | 7/2001 | Krivosha et al. | |
| 2003/0032908 A1 | * 2/2003 | Nafya ............................ | 602/27 |

* cited by examiner

*Primary Examiner*—Michael A. Brown

(57) ABSTRACT

An ankle apparatus for a person with a paralytic foot includes a body with a free end and a connector end, and a support portion with a rear wall. The support portion extends between the free end and the connector end. Two spaced apart side panels extend down from the connector end and are angled away from each other in a direction leading away from the rear wall. Another body, orthogonal to the first body, has a free and, a connector end, and a support portion, which extends between the free end and the connector end. The second support portion cooperates with the foot and the two connector ends are connected to restrict relative movement of two bodies.

16 Claims, 2 Drawing Sheets

ANKLE SUPPORT

FIELD OF THE INVENTION

The present invention concerns ankle supports, more particularly to ankle supports for use primarily by hemiplegics, or any person with a paralytic foot.

BACKGROUND OF THE INVENTION

Hemiplegics suffer from paralysis on one side of the body. Typically, this type of paralysis results in loss of motor function in one arm or one leg or both limbs on the same side of the body. The extent of the loss of limb function depends upon the severity of the brain injury causing the paralysis. In the case of paralysis of the leg, the hemiplegic often loses some or all coordination of the foot, resulting in so-called foot-drop. The foot, if not restrained may be prone to injury and may severely limit the mobility of the hemiplegic. Generally speaking, the hemiplegic uses an orthopedic apparatus, which, in most cases includes a foot support connected to an ankle support for immobilizing the foot. Many designs of orthopedic devices exist, some of which are exemplified in the following:

- U.S. Pat. No. 4,289,122, issued Sep. 15, 1981 to Mason for "Ankle-Foot Orthosis";
- U.S. Pat. No. 4,982,733, issued Jan. 8, 1991 to Broadhurst for "Sub-Talar Stabilizer Ankle Brace";
- U.S. Pat. No. 5,527,269, issued Jun. 18, 1996 to Reithofer for "Ankle Joint Orthesis";
- U.S. Pat. No. 5,376,068, issued Dec. 27, 1994 to Grifka for "Ankle Joint Brace";
- U.S. Pat. No. 4,517,968, issued May 21, 1985 to Greene for "Composite Orthosis For Ankle Sprains and the like";
- U.S. Pat. No. 4,646,726, issued Mar. 3, 1987 to Westin for "Ankle Joint Orthosis";
- U.S. Pat. No. 4,955,370, issued Sep. 11, 1990 to Pettine for "Achilles Tendon Rehabilitation Brace And Method For Its Manufacture"; and
- U.S. Pat. No. 5,700,237, issued Dec. 23, 1997 to Hess for "Device For Correcting Ankle Contractures".

The above designs, however, suffer from a number of significant drawbacks. Many of aforesaid designs include complex strap systems to secure the support to the foot, the lower part of the leg and/or the ankle. This complexity may be inappropriate for use by a hemiplegic or a person with a paralytic foot. By securing the lower part of the leg to the support, the latter prevent any dorsal flexion of the ankle and of the knee as would normally occur during walking, thereby forcing the user to have a pronounced lateral displacement of the basin inducing an extended abduction movement of the hip articulation to avoid the foot to likely hit the ground during its forward displacement relative thereto. In a long run this will cause other articulation problems to the user away from the ankle. By eliminating the possible dorsal flexion of the ankle and the knee of the user, the apparatus will force the entire body of the user to fall either forward or on the side in case of lost of his/her equilibrium, as opposed to allow the user to have his/her body to simply fall off when the dorsal flexions are possible. Furthermore, by eliminating the dorsal flexion of the ankle, the apparatus prevents the user from moving his/her foot and feeling that movement which are both very useful for the proper rehabilitation of the locomotive function of the user.

To get around this, some apparatuses include a pivot axis to allow the flexion of the foot. In order to be efficient and comfortable to the user, such a pivot axis needs to be properly aligned with the natural ankle axis of the user, which increases the size and complexity of the apparatus that generally needs to be used in cooperation with an orthopedic shoe.

Moreover, the complex strap systems may prevent the design's use with conventional shoes and may often not be aesthetically pleasing to the user.

Furthermore, some designs may require additional pieces to enable the support to be comfortably used for extended periods of time. In addition, some designs appear to completely immobilize the lower part of the leg and ankle, which may limit their use to people with sprains or bone breakages and the like.

Furthermore, the sole portion of the apparatuses generally supports the entire length of the foot, thereby constraining the dorsal flexion of the metatarsus and the toes and creating some discomfort to the user.

Thus there is a need for an improved orthopedic ankle support.

SUMMARY OF THE INVENTION

The present invention reduces the difficulties and disadvantages of the prior art by providing an ankle support for use by hemiplegics suffering from ankle instability. The ankle support provides a semi-rigid support, which enables the user to maintain the correct form of the foot and ankle, while significantly reducing downwards and lateral movement of the foot relative to the ankle (inversion and eversion movements of the ankle), and allowing the lower portion of the leg to slightly move away from the support without disengaging therefrom. Advantageously, the movement restriction significantly reduces or essentially eliminates the discomfort that occurred with most of the aforesaid designs and enables the apparatus to be worn for a significantly longer time. In addition, the apparatus is adaptable for use with both feet and is designed to fit unobtrusively in a user's shoe, and does not need to be secured to the user. Accordingly, the sole portion of the present apparatus generally extends from the heel to an area adjacent the metatarsals of the user's foot, generally at the base of the widest area of the foot, such that the ball of the foot is totally free to flex during walking movement. Furthermore, a pair of resilient braces conforms to the user's foot when the shoelaces are tightened, thereby improving the comfort and the efficiency of the apparatus and the cooperation of the apparatus to the ankle region of the user for better movement interaction with the shoe. The apparatus is simple to use and inexpensive to manufacture from readily available materials and eliminates the need for complex strap systems.

Aesthetically, a large proportion, including the lateral brace straps, of the apparatus of the present invention is intended to be generally hidden by the shoe of the user while the upper portion, including the side panels, supporting the lower portion of the leg is generally not visible by someone looking at the user from the front.

In accordance with an embodiment of the present invention, there is provided an ankle support apparatus for use by a person having a paralytic foot, said apparatus comprising: a first body having a first free end portion and a first connector end portion, and a first support portion having a rear wall, said first support portion extending between said first free end portion and said first connector end portion, said first support portion being cooperable with an Achilles tendon of said paralytic foot; a pair of spaced apart side panels extending downwardly from said first connector end portion, said side panels being angled away from each other in a direction leading away from said rear wall; a second body having a second free end portion and a second connector end portion, and a second support portion extending between said second free end portion and said second connector end portion, said second support portion being cooperable with said paralytic foot; said first and second connector end portions being connected to each other to restrict the movement of said second body relative to said first body, said first and second bodies being disposed generally orthogonal relative to each other.

Typically, the first support portion further includes a pair of spaced apart sidewalls, said rear wall interconnecting said spaced apart sidewalls to define an inner surface configured and sized to cooperate with said Achilles tendon and lie against the sides of a lower leg portion. Each of said side panels has a connector point located thereon adjacent said first connector end portion.

Typically, the rear wall includes a concave cutaway portion located between said spaced apart side panels, said cutaway portion being sized and shaped to lie snuggly against the heel. The second support portion includes a rearwardly disposed heel portion, said second support portion being configured and sized to extend from said heel portion and to an area adjacent the metatarsals of the foot. The second support portion is substantially planar.

Typically, the second support portion includes a first cushion attached thereto for supporting a portion of the foot thereon.

Typically, the second body includes a sole having two intermediate connector portions adjacent said second free end portion.

In one embodiment, the apparatus further includes a pair of brace straps, each brace strap having respective brace strap connector ends. Each of said brace strap connector ends are respectively connected to said intermediate connector portions and to said connector points. The brace straps are made from a material of sufficient resiliency to allow said brace straps to attain the form of a user's paralytic foot, said second body being configured and sized to fit inside a shoe of said user, said shoe being tightenable to compress said brace straps around said paralytic foot and ankle.

Typically, said first body and said second body are formed from a single piece of moldable material. Typically, said first body is open to allow movement of said lower leg portion away from and towards said first body.

BRIEF DESCRIPTION OF THE DRAWINGS

Further aspects and advantages of the present invention will become better understood with reference to the description in association with the following Figures, wherein.

DETAILED DESCRIPTION OF THE PREFERRED EMBODIMENTS

Figure 1:
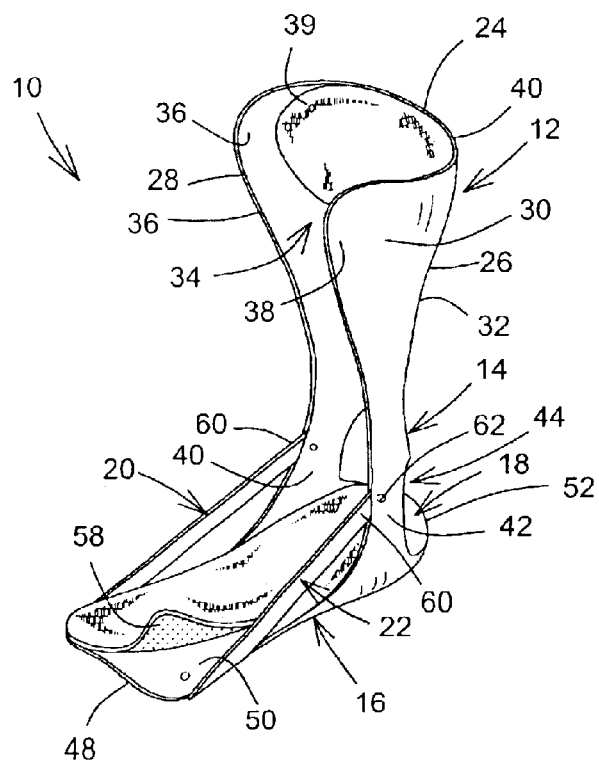
FIG. 1 is a simplified perspective view of an embodiment of an ankle support in accordance with the present invention.

Referring now to FIG. 1, an embodiment of a one-piece ankle support apparatus in accordance with the present invention for use by a hemiplegic, or by a person suffering of a paralytic foot, is illustrated generally at 10. Broadly speaking, the ankle support apparatus 10 includes a first body 12 with a first connector end portion 14, a second body 16 with a second connector end portion 18, and a pair of brace straps 20, 22.

Figure 2:
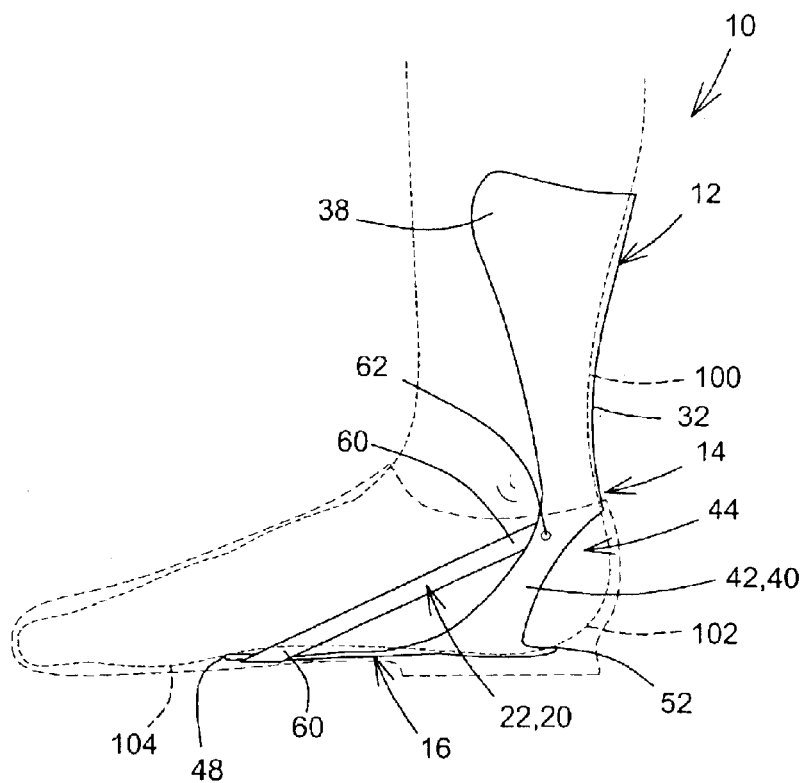
FIG. 2 is a simplified side view of the ankle support of FIG. 1, showing the position of the ankle, the foot and the shoe in relation therewith.
Figure 3:
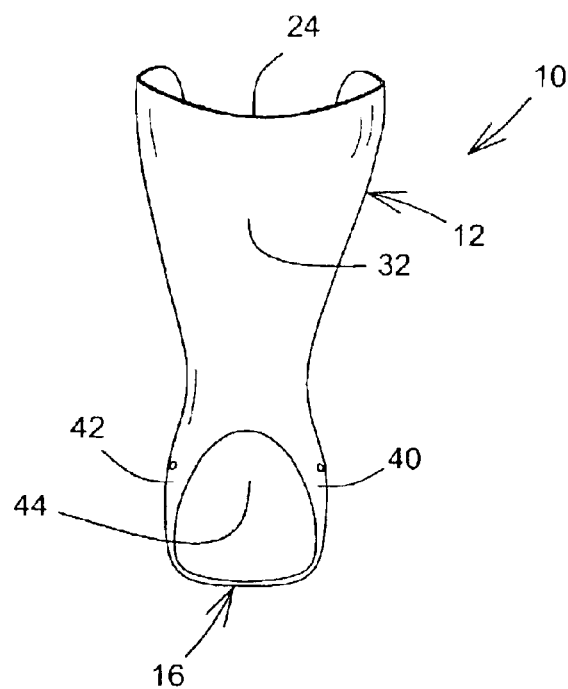
FIG. 3 is a simplified rear view of the ankle support of FIG. 1.

Referring now to FIGS. 1, 2 and 3, the first body 12 includes a first free end portion 24 and a first support portion 26 which extends between the free end portion 24 and the first connector end portion 14. The first support portion 26 includes a pair of spaced apart sidewalls 28, 30 and a rear wall 32 interconnecting the spaced apart sidewalls 28, 30. The sidewalls 28, 30 and the rear wall 32 define an inner surface 34, which is sized and configured or shaped to cooperate with the Achilles tendon 100. A pair of projections 36, 38 are connected to and extend away from the sidewalls 28, 30 and are molded to lie against the sides of a lower leg portion. The rear wall 32 is also molded to conform to the lower part of the calf muscle. For greater comfort, a cushion 39 may be connected to an upper part 40 of the rear wall 32.

The first connector end portion 14 includes a pair of side panels 40, 42, which are connected to the second connector end portion 18. Due to the shape and orientation of the ankle and the lower leg, the side panels 40, 42 are angled away from each other in a direction leading away from the rear wall 32 and the heel 102. As best illustrated in FIGS. 2 and 3, a concave cutaway portion 44 is located between the side panels 40, 42. The concave portion 44 is shaped and sized to lie snuggly against the heel 102.

Referring now to FIGS. 1 and 2, the second body 16 includes a second free end portion 48 and a second support portion 50 which extends between the second free end portion 48 and the second connector end portion 18. The second support portion 50 includes a rearwardly disposed heel portion 52 over which the heel 102 rests. Typically, the first body 12 and second body 16 are disposed generally orthogonal to each other, with an angle typically of about ninety-five degrees (95°).

As best illustrated in FIG. 2, the side panels 40, 42 extend downwardly from the first connector end portion 14 and are connected respectively to on either side of the heel portion 52.

Figure 4:
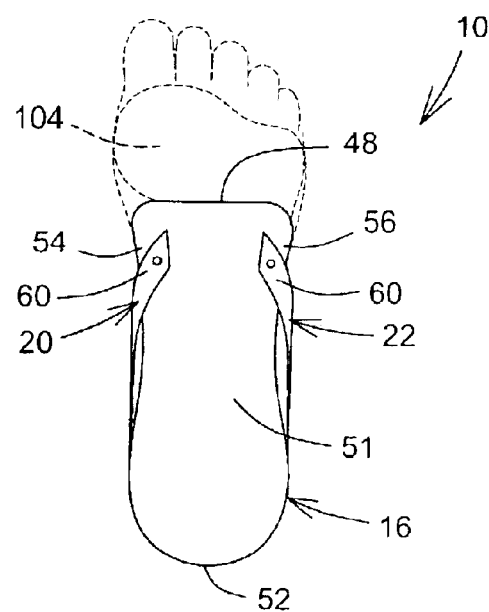
FIG. 4 is a simplified bottom view of the ankle support of FIG. 1, showing the position of the foot in relation therewith.

As best illustrated in FIG. 4, the second body 16 includes a sole 51 with two intermediate connector portions 54, 56. As best illustrated in FIGS. 2 and 4, the second body 16 is configured and sized to extend from the heel 102 to an area, the ball of the left foot, adjacent the foot print of the metatarsals 104 so as to allow free movement thereof during its dorsal flexion occurring during normal walking movement.

Referring now to FIGS. 1, 2, and 3, the second support portion 50 is a substantially planar sheet of material which together with the rearwardly disposed heel portion 52, the side panels 40, 42 and the shaped first body 12 cooperate and to conform with the shape of a hemiplegic's foot and lower leg. This allows the hemiplegic's lower leg to move away from and towards the first body 12, while restricting downwards movement of the foot.

If desired, a cushion 58 can be used to cover substantially the entire surface area of the second support portion 50. The cushion 58 can be temporarily adhered to the second support portion 50 or it may be adhered thereto using an adhesive.

The brace straps 20, 22 both include respective brace strap connector ends 60, which are connected to the intermediate connector portions 54, 56, typically located at a position adjacent the second free end portion 48, and to a pair of connector points 62 located on the side panels 40, 42, typically adjacent the first connector end portion 14.

The brace straps 20, 22 further restrict downward movement the second body 16 away from the first body 12 or rearward movement of the first body 12 away from the second body 16. This restricted movement of the second body 16 relative to the first body 12 follows the normal motion of the foot (dorsal flexion) and ankle during walking and the like activities, but reduces foot drop and twisting of the foot relative to the ankle. Typically, both brace straps 20, 22 work simultaneously in tension against the plantar flexion of the foot to reduce the so-called foot drop, while they work independently in isolation from each other against the twisting movements of the foot (left foot shown in FIG. 4) and the ankle, the twisting movement being either an inversion movement of the ankle (tension in the outside brace strap 22 shown in FIG. 4) or an eversion movement of the ankle (tension in the inside brace strap 20 shown in FIG. 4).

The brace straps 20, 22 are typically made from a material that is resistant in tension and typically flexible in compression, which restricts movement of the second body 16 away from the first body 12. In this embodiment, the brace member straps 20, 22 are made from strips of leather or the like.

The bodies 12 and 14 are typically made of a moldable smooth plastic material that allows the apparatus 10 to be inexpensively custom-made to any desired foot size and ankle size. Typically, the apparatus 10 can be used with either foot.

Operation

The apparatus 10 is typically supplied as illustrated in FIG. 1. Referring to FIG. 2, with the apparatus in the default first position, the Achilles tendon 100 and the metatarsals of the foot 104 are located adjacent the respective first and second bodies 12, 16. The heel portion 102 of the foot is slid rearwardly to cooperate with the heel portion 52. When the foot is comfortably located, the apparatus 10 restricts the movement of the foot from the orthogonal configuration towards the first body 12, while allowing the lower part of the leg to move away from the first body 12 to allow a natural walking movement. For hemiplegics with residual mobility, the brace straps 20, 22 support the ankle and the foot to allow normal walking movements with no unusual induced twisting of the hip articulation without the risk of foot drop, which may cause the hemiplegic to trip and fall or ankle twisting, which could cause injury to the tendons of the ankle.

The apparatus 10 is typically configured and sized to be accommodated in a conventional shoe either above or typically underneath a removable sole, which when the shoe is tightened, by laces, zippers or buckles and the like, the side panels 40, 42 and the brace straps 20, 22 conform to the shape of the ankle and provide a tight, yet comfortable fit.

What is claimed is:

1. An ankle support apparatus for use by a person having a paralytic foot, said apparatus comprising:
   a first body having a first free end portion and a first connector end portion, and a first support portion having a rear wall, said first support portion extending between said first free end portion and said first connector end portion, said first support portion being cooperable with an Achilles tendon of said paralytic foot;
   a pair of spaced apart side panels extending downwardly from said first connector end portion, said side panels being angled away from each other in a direction leading away from said rear wall;
   a second body having a second free end portion and a second connector end portion, and a second support portion extending between said second free end portion and said second connector end portion, said second support portion being cooperable with said paralytic foot;
   said first and second connector end portions being connected to each other to restrict the movement of said second body relative to said first body, said first and second bodies being disposed generally orthogonal relative to each other.

2. The apparatus, according to claim 1, in which said first support portion further includes a pair of spaced apart sidewalls, said rear wall interconnecting said spaced apart sidewalls to define an inner surface configured and sized to cooperate with said Achilles tendon and lie against the sides of a lower leg portion.

3. The apparatus, according to claim 2, in which each of said side panels has a connector point located thereon adjacent said first connector end portion.

4. The apparatus, according to claim 3, in which said rear wall includes a concave cutaway portion located between said spaced apart side panels, said cutaway portion being sized and shaped to lie snuggly against the heel.

5. The apparatus, according to claim 4, in which said second support portion includes a rearwardly disposed heel portion, said second support portion being configured and sized to extend from said heel portion and to an area adjacent the metatarsals of the foot.

6. The apparatus, according to claim 5, in which said second support portion is substantially planar.

7. The apparatus, according to claim 6, in which said second support portion includes a first cushion attached thereto for supporting a portion of the foot thereon.

8. The apparatus, according to claim 7, in which said second body includes a sole having two intermediate connector portions adjacent said second free end portion.

9. The apparatus, according to claim 8, further including a pair of brace straps, each brace strap having respective brace strap connector ends.

10. The apparatus, according to claim 9, in which each of said brace strap connector ends arm respectively connected to said intermediate connector portions and to said connector points.

11. The apparatus, according to claim 10, in which said brace straps are made from a material of sufficient resiliency to allow said brace straps to attain the form of a user's paralytic foot, said second body being configured and sized to fit inside a shoe of said user, said shoe being tightenable to compress said brace straps around said paralytic foot and ankle.

12. The apparatus, according to claim 2, in which a second cushion is connected to an upper part of said rear wall for removably receiving a lower leg portion of the user thereagainst.

13. The apparatus, according to claim 12, in which said first body is open to allow movement of said lower leg portion away from and towards said first body.

14. The apparatus, according to claim 1, further including a pair of brace straps, each brace strap having respective brace strap connector ends, each of sold brace strap connector ends being respectively connected to said first and second bodies.

15. The apparatus, according to claim 14, in which each of said brace strap connector ends is respectively connected to said first and second bodies adjacent said first connector end portion and said second free end portion, respectively.

16. The apparatus, according to claim 1, in which said first body and said second body are formed from a single piece of moldable material.

* * * * *